United States Patent [19]
Wissler et al.

[11] Patent Number: 6,087,123
[45] Date of Patent: *Jul. 11, 2000

[54] METAL-CONTAINING RIBONUCLEOTIDE POLYPEPTIDES

[75] Inventors: Josef Wissler, Bad Nauheim; Enno Logemann, Freiburg; Stefan Kiesewetter, Lautertal-Unterlauter; Ludwig Heilmeyer, Bochum, all of Germany

[73] Assignee: Fraunhofer-Gesellschaft zur Foerderung der Angewandten Forschung e.V., Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/794,000

[22] PCT Filed: Jul. 17, 1996

[86] PCT No.: PCT/DE96/01337

§ 371 Date: Sep. 19, 1997

§ 102(e) Date: Sep. 19, 1997

[87] PCT Pub. No.: WO97/04007

PCT Pub. Date: Feb. 6, 1997

[30] Foreign Application Priority Data

Jul. 17, 1995 [DE] Germany ............................ 195 25 992
Aug. 18, 1995 [DE] Germany ............................ 195 30 500

[51] Int. Cl.$^7$ ............................ C12N 15/00; C12P 19/34; C07K 1/14; C07H 21/04
[52] U.S. Cl. ............................ 435/69.1; 435/6; 435/91.1; 435/91.3; 530/300; 530/324; 530/412; 536/23.1; 536/23.5
[58] Field of Search ............................ 435/6, 69.1, 70.1, 435/91.1, 91.3, 91.5, 91.51, 375; 530/300, 414, 324, 412, 416, 417, 418; 536/22.1, 23.1, 24.3, 24.31, 24.5; 514/44

[56] References Cited

PUBLICATIONS

Lloyd, A.W. DDT, vol. 2, No. 10, pp. 397–398 (Oct. 1997).

Journal of Biological Chemistry; "Primary Structure and Binding Properties of Calgranulin C, a Nove. S100–like Calcium–binding Protein from Pig Granulocytes"; Bd. 269, Nr. 46, Nov. 18, 1994; Baltimore, MD US Biochem. Eng., [Int. Congr.] (1987) Meeting Date 1986,.

1.385–9 "An endogenous bioactive metallo–ribonucleo–polypeptide: A copper–containing monocytic blood vessel morphogen as novel type of wound–hormone" Chemical Abstracts, vol. 106, No. 3, Jan. 19, 1987; Columbus, Ohio, US; Abstract No. 16813.

Indian Journal of Medical Research, "Isolation & characterization of tumour angiogenesis factor from solid tumours & body fluids from cancer patients" bd. 90, Aug. 1989, Deshpande et al.

*Primary Examiner*—George C. Elliott
*Assistant Examiner*—Mark L. Shibuya
*Attorney, Agent, or Firm*—Marshall & Melhorn

[57] ABSTRACT

The invention relates to bioactive ribonucleo polypeptides (RNP) containing copper, zinc or calcium. These are non-mitogenic morphogens for blood vessels of a defined primary structure for intercellular communication with genetic information. Zn/Ca/Cu-RNP can enzymatically hydrolyse nucleinic acids in a regulated manner (regulated nuclease activity) and be modulated and regulated via Zn/Ca/Cu-metal ion contents as "molecular switches" in mutual bioactivity. The compounds selectively stimulate the directional growth of the morphogenesis of blood vessels in vivo and in vitro and lead to neovascularisation of tissues. The invention further relates to a method of producing and obtaining the RNP as well as its utilisation, and medicines.

46 Claims, No Drawings

METAL-CONTAINING RIBONUCLEOTIDE POLYPEPTIDES

RELATED APPLICATIONS

This is the national stage filing under 35 U.S.C. § 371 of PCT application, PCT/DE96/01337, filed Jun. 14, 1996. The PCT application, PCT/DE96/01337, is hereby incorporated by reference.

The present invention relates to metal-containing ribonucleotide polypeptides (RNP) and to a method for their manufacture, their utilisation and medicines containing ribonucleotide polypeptides or antibodies against ribonucleotide polypeptides and/or their biomolecular equivalent structures and/or portions and/or derivates.

Homeostasis of the tissue of the body, its organs and tissues is dependent on regulatory mechanisms of angiogenesis (lateral and directional growth of the blood vessel capillaries). It influences both tissue repair and wound healing, new tissue formation and embryogenesis and the reproductive cycles as well as accumulation, restitution and destruction of tumours, transplants and tissues, both supplied with, and free of vessels.

Until now, no non-mitogenic mediators have been discovered by whose means an influence can be exerted on tissue homeostasis, i.e. induction and regulation of vessel growth.

The object of the present invention is therefore to prepare a non-mitogenic mediator of tissue homeostasis, by means of which principally tissue repair, wound healing, angiogenesis and neovascularisation can be influenced. A further object of the invention is preparation of a method for manufacturing the non-mitogenic mediators and a medicine, containing this non-mitogenic mediator.

This object is fulfilled by a bioactive ribonucleotide polypeptide according to Patent claim 1, by a method according to Patent claims 5 or 26, by a medicine according to Patent claims 28 or 29 and by utilisation according to Patent claims 30 or 31.

It was discovered by the inventors that there are non-mitogenic cellular mediators on a nucleinic acid basis with a defined sequence, which can specifically cause the formation of blood vessels in vivo and in vitro, and represent biologically specific, naturally-acting non-mitogenic mediators of angiogenesis or of directional growth of blood vessel shoots.

The new class of cellular morphogens for endothelial cells indicated for the first time by the inventors exists in the form of bioactive metal-ribonucleotide peptides (RNP). The metal can preferably be calcium, copper or zinc.

In the RNA portion they contain among other things the following sequence of nucleotides or portions or derivates thereof:

AAAGAGAAAGCUGCUCCGAAGNCAG (SEQ ID NO:1).

in the protein portion they contain among other things the following protein sequence:

NH$_2$-TKLEDHLEGIINIFHQYSVRLG (SEQ ID NO:3)

HYDTLIKRELKQLITKELPNTLKN

TKDQGTIDKIFQNLDANQDEQVSF

KEFVVLVTDVLITAHDNIHKE-COOH

According to the invention the sequences are intended to be so understood that RNP also come under this category, in which in the RNA portion and/or protein portion exchanges of nucleotides and/or amino acids have taken place compared to the sequences shown above, or that only portions of the above sequences are present.

The invention also relates to DNA, coding for the above-named amino acids, the DNA comprising:

(a) the following DNA or a DNA differing therefrom by one or a plurality of base pairs,

```
                              Reverse translated 1-91
   T==K==L==E==D==H==L==E==G==I==I==N==I==F==H==Q==Y==S20V==(SEQ ID NO:3)
   ACCAAGCGGAGGACCACCTGGAGGGCAT-
   CATCAACATCCCCCACCAGTACTCTGTGCGG L==G==H==Y==D==T==L==I==K==R==E==L==K==Q==L==I==T==K40E==L
   CTGGGCCACTATGACACCCTGAT-
   CAAGCGGGAGCTGAAGCAGCTGATCACCAAGGAGCTG P==N==T==L==K==N==T==K==D==Q==G==T==I==D==K==I==F==G60N==L
   CCCAACACCCTGAAGAACACCAAGGAC-
   CAGGGCACCATTGACAAGATCTTCCAGAACCTG D==A==N==Q==D==E==Q==V==S==F==K==E==F==V==V==L==V==T80D==V
   GATGCCAACCAGGATGAGCAGGTGTCCT-
   CAAGGAGTTTGTGGCTGGTGACAGATGTG L==I==T==A==H==D==N==I==H==K==E                              91
   CTGATCACAGCCCATGACAACATCCACAAGGAG
``` or (b) DNA hydridising with the DNA of (a), or (c) a DNA related to the DNA of (a) or (b) via the degenerated genetic code.

The nucleotides contained in the RNA portion were translated into DNA:

RNA/DNA

AAAGAGAAAGCNGCNGCNCCGAAGNCAG (SEQ ID NO:4)

CTGNCTTCGGNGCNGCTTTCTCTTT

The RNP according to the invention are further characterised by the following properties:

a) biological effects in vitro and in vivo:
- cell selective morphogenic action in vitro on isolated, primary and/or cloned blood capillary endothelial cells in the culture for non-mitogenic induction of the alteration of the cell phenotype from the confluent condition, for non-mitogenic alteration and increase in the cell migration capacity and for non-mitogenic alteration of the spatiotemperal supraceluar organisation of the cells for three-dimensional organoid structures similar to capillaries in the cultures;
- specific chemotropic action on blood vessels in vivo;
- induction of a directional growth (chemotropism) of blood vessels in vivo;
- during the sprouting stage in vivo the points of the growing capillaries have increased permeability;
- induction of a neovascularisation of tissues by directed ingrowth of blood vessels;
- $LD_{50}$ not determinable, as no lethal effects;
- no mobilisation of adult or juvenile leucocytes (no leucocytosis or left displacement reactions) in vivo;
- no direct activity on smooth musculature in vivo;
- no spasmogenic activity on smooth musculature in vitro;
- no spasmogenic activity on striped musculature in vitro;
- no actions identical to endotoxins or similar thereto in vivo and in vitro;
- no chemical attraction (chemotaxis) of leucocytes in vitro;
- no positive or negative chemokinetic action on leucocytes in vitro;
- no phagocytosis-stimulating action on leycocytes in vitro;
- no visible shock effects or systemically deleterious effects of the instantaneous type or protracted type in the overall organism in vivo;
- no lysis effects on erythrocytes, thrombocytes, endothelial cells and fibroblasts in vitro;
- no significant pyrogenic action in vivo;
- no direct increase in capillary permeability in the skin test in viva;
- no mitogenic effect on leucocytes, fibroblasts and endothelial cells in vitro;
- Zn/Cu/Ca-RNP can develop regulated and selective nuclease effect, and can be modulated and regulated in their mutual bioactivity via Zn/Cu/Ca-Metal ion components as "molecular switches".

b) physical-chemical and chemical-structural properties:
- typical properties of a ribonucleinic acid (RNA) in the complex of the RNP with polypeptide (protein) and copper, zinc and calcium ions,
- typical protein properties and protein reactions of the polypeptide portion (foline and biuret reaction) in the complex of the RNP with RNA and copper, zinc and calcium ions,
- melting point: approximately 200° C. (air and oxygen excluded);
- during hydrolysis e.g. of CuRNP in 5NHCl, 150° C., 1 hour, the copper ion is released and can be separated as a yellow, blackening copper-1-oxide;
- they can arise as cellular mediators;
- electrophoretic migration at pH 7.40 in acrylamide matrices; anodic or as wide distribution over the whole path (anomalous hydrodynamic behaviour);
- soluble in aqueous media inclusive of 20% ethanol at a pH value of at least 4.0 to 10;
- constant temperature coefficient of solubility in ammonium sulphate solutions between −10° C. and +50° C.;
- among other things they contain the amino acids in the polypeptide portion of the RNP: alanine (A), asparagenic acid (D), glutamic acid (E), glycine (G), isoleucine (I), lysin (K), leucine (L), proline (P), arginine (R), serine (S), theonine (T), valine (V), tyrosine (Y);
- they are blocked at the 5' end of the nucleotide sequence in the RNA portion of the RNP by a phosphate residue;
- they contain at least one copper ion in the RNP complex;
- they contain modified bases in the RNA portion of the RNP, of which at least one can be represented by isoguanosine;
- adsorption spectrum (UV, visible and close IR range) typical for nucleinic acid ($E_{260}$ nm $\geq E_{280}$ nm);
- molecular mass of the native RNP (primary structure): about 40,000 Daltons (lowest common multiple of the RNP components);
- no protein quaternary structure in the protein portion of the RNP in the form of physically bonded peptide sub-units; the native protein consists only of a peptide unit (lowest common denominator of the RNP unit);
- soluble in an ammonium sulphate solution at a saturation of 90% (3.6 mol/l);
- they behave hydrodynamically abnormally, so that the hydrodynamic equivalent of the molecular mass appears about 20 times smaller than the actual molecular mass of the components in the form of the lowest common denominator of the components, as far as can be determined by gel chromatographic, electrophoretic and membrane methods;
- they therefore permeate through membranes with a nominal retention threshold of >1000 Daltons;
- they adsorb reversibly in structure and biological activity on anion and cation exchangers, calcium phosphate gel and hydroxylapatite and can be natively subjected to volume distribution chromatography.

The bioactive RNP of the invention are cellular inflammation and wound healing mediators with topobiochemically and biologically specific action. Their biological purpose is the induction and regulation of non-mitogenic vessel directional growth. This can lead to neovascularisation of tissue. They originate in vitro during the culture of leucocytes or in vivo during the accumulation of leucocytes at the locus of inflammation in addition to a plurality of other hormones and mediators.

The bioactive RNP morphogens produced and obtained according to the invention represent high-value body-specific agents. They may for example be used for influencing the vascular status of tissues (e.g. heart muscle tissue, skeletal muscle tissue, lungs, wound healing, reproductive cycles, embryogenesis and transplants). A further possible use is the production of inhibitors of undesired angiogenesis and neovascularisation of tissues in the case of pathological phenomena in tuberculosis, diabetes, tumours, reproductive cycles and tissue transplants. As paracrinically acting mediators they can transmit ("shuttle") genetic information from cell to cell. Thus they can also be used in gene biotechnology for transmitting genetic information with an optimised nucleinic acid ingredient ("horizontal transfer") and with enzymatic actions (nuclease activity) for influencing the content of nucleinic acid, and cellular functions (e.g. differentiation).

The bioactive RNP morphogens according to the invention may be given individually or as a mixture in the form of conventional medicines locally in the case of mammals, e.g. human beings, in a quantity of >1 fmol in concentration >10 pmol/l. The threshold dose for effectiveness in vivo comes to >50 fmol, preferably 2.5 fmol. These medicines are suitable for specifically influencing angiomorphogenesis and the vascular condition of the tissue of a body of a mammal. These medicines, in order to fulfil the same purposes, may also contain at least one anti-RNP immunoglobulin and/or biomolecular equivalent structures.

Another object of the invention is a method of manufacturing and obtaining the bioactive RNP morphogens of the cells of the reticulo-endothelial system, of leucocytes and of inflammation tissue, which is characterised in that the cells, e.g. leucocytes or inflammation tissue are homogenised or leucocytes are cultivated and the resultant RNP morphogens are obtained from the homogenates or from the residual culture solution.

It is basically also possible to prepare the cells, e.g. leucocytes, or mediators directly without culture.

Culture of the cells (leucocytes) can be carried out basically in any medium containing the cells (leucocytes).

For the culture of cells such as leucocytes, there is normally added to the culture media, at a planned duration of the culture of over 1 hour, serum, for example calf serum or horse serum, as the serum ingredients are favourable for maintaining the life functions of the cells. If however the serum-containing culture solution is to be prepared on proteins (mediators), which are generated by the culture, obtaining the product proteins, which are normally only present in small concentrations, this presents great difficulties due to the plurality of foreign proteins originating from the serum. Moreover, it cannot be ascertained with certainty whether a specific mediator is of humoral or cellular origin and from which species it originates, i.e. whether it is a mediator of the species whose cells have been cultivated or of the species from which the serum used (mostly heterologous) originates.

The fully-synthetic cell culture medium preferably used according to the invention contains the conventional groups of materials, such as salts, sugars, amino acids, nucleosides and nucleoside bases, vitamins, vitaminoids, coenzymes and/or steroids in an aqueous solution. It is characterised in that in addition it contains one or a mixture of a plurality of materials which have proved particularly valuable for the life capacity and growth of the leucocytes and their capacity for producing mediators. Among these materials there belong unsaturated fatty acids, flavonoids, ubiquinones, vitamin C and mevalolacton.

The cell culture medium for longer-term cell or leucocyte culture is preferably used without the addition of serum. Instead of this it receives at least one defined protein, which in a particularly preferred embodiment is high-purity, molecularly uniform serum albumin.

In further preferred embodiments, the fully synthetic serum-free cell culture medium used according to the invention can also contain further compounds, favourable to the culture of leucocytes, from the classes of materials of the polyhydroxy compounds and sugar, amino acids, nucleosides, anionic compounds and/or vitamins, whose use is not conventional in known culture media. The ingredients of the medium used according to the invention are in quantities so co-ordinated in ratio to one another that the concentration of the components in the medium is largely adapted to the natural concentration ranges of the plasma; cf. Ciba-Geigy AG (publisher) (1969) in Documenta Geigy, Wissenschaftliche Tabellen [Scientific Tables] edition Geigy S. A., Basle.

Preferably the cell culture medium is free of tensides, heavy metal salts and pigments, which damage the cells and can disrupt production of the desired cell products from the culture solution.

Particularly preferred for culture of the cells-leucocytes in the method according to the invention is the cell culture medium with the composition indicated In order to produce the medium, water with the ATM-1 quality is used; cf.ASTM D-1193-70 Standard Specification for Reagent Water 1970; Annual Book of ASTM-Standards, Easton Maryland, ASTM 1970. In addition it is freed of possible endotoxin contaminations by ultrafiltration on tenside-free membranes with an exclusion threshold of 10000 Daltons.

The finished medium is filter-sterilised on tenside-free membranes with $\geq 0.2$ μm pore size.

TABLE 1

| Nr. | Component | mol/l |
|-----|-----------|-------|
| 1 | KCl | 5.0 m |
| 2 | KH$_2$PO$_4$ | 0.2 m |
| 3 | NaCl | 120.0 m |
| 4 | Na$_2$HPO$_4$ | 0.8 m |
| 5 | Na$_2$SO$_4$ | 0.2 m |
| 6 | L-Ascorbic acid | 0.2 m |
| 7 | Cholin chloride | 50.0 μ |
| 8 | 2-Desoxy-D-ribose | 5.0 μ |
| 9 | D-Galactose | 0.5 m |
| 10 | D-Glucose | 5.0 m |
| 11 | D-Glucurono-γ-lacton | 0.1 m |
| 12 | Glycerine | 50.0 μ |
| 13 | myo-Inosite | 0.5 m |
| 14 | Na-Acetate | 0.2 m |
| 15 | Na-Citrate | 50.0 μ |
| 16 | Na-Pyruvate | 0.1 m |
| 17 | D-Ribose | 20.0 μ |
| 18 | Succinic acid | 0.1 m |
| 19 | xylite | 10.0 μ |
| 20 | D-Xylose | 20.0 μ |
| 21 | CaCl$_2$ | 2.0 m |
| 22 | MgCl$_2$ | 1.0 m |
| 23 | NaHCO$_3$ | 10.0 m |
| 24 | Human serum albumin | 7.7 μ |
| 25 | Penicillin | 1.0 μ |
| 26 | Streptomycin | 1.0 μ |
| 27 | L-Glutamine | 1.0 m |
| 28 | L-Alanine | 0.2 m |
| 29 | L-Asparagine | 0.1 m |
| 30 | L-aspartic acid | 0.1 m |
| 31 | L-glutamic acid | 0.1 m |
| 32 | glycine | 0.2 m |
| 33 | L-proline | 0.1 m |
| 34 | L-serine | 0.1 m |
| 35 | L-arginine | 0.4 m |
| 36 | 4-aminobenzoic acid | 2.0 μ |
| 37 | L-cysteine | 0.2 m |
| 38 | L-hstidine | 0.1 m |
| 39 | L-hydroxyproline | 10.0 μ |
| 40 | L-isoleucine | 0.2 m |
| 41 | L-leucine | 0.2 m |
| 42 | L-lysine-HCl | 0.2 m |
| 43 | L-methionine | 0.1 m |
| 44 | L-ornithine | 50.0 μ |
| 45 | L-phenylalanine | 0.1 m |
| 46 | sarcosine | 50.0 μ |
| 47 | taurine | 0.1 m |
| 48 | L-threonine | 0.2 m |
| 49 | L-trypthophane | 50.0 μ |
| 50 | L-tyrosine | 0.1 m |
| 51 | -valine | 0.2 m |
| 52 | glutathion reduced | 3.0 μ |

TABLE 1-continued

| Nr. | Component | mol/1 |
|---|---|---|
| 53 | carnosine | 5.0 μ |
| 54 | mevalolactone | 5.0 μ |
| 55 | adenine | 50.0 μ |
| 56 | adenosine | 50.0 μ |
| 57 | cytidine | 50.0 μ |
| 58 | guanine | 5.0 μ |
| 59 | guanosine | 20.0 μ |
| 60 | hypoxanthine | 5.0 μ |
| 61 | 5-methylcytosine | 5.0 μ |
| 62 | thymidine | 20.0 μ |
| 63 | thymine | 5.0 μ |
| 64 | uracil | 5.0 μ |
| 65 | uridine | 20.0 μ |
| 66 | xanthine | 5.0 μ |
| 67 | biotine | 1.0 μ |
| 68 | D-Ca-pantothenate | 5.0 |
| 69 | ergocalciferol | 0.5 μ |
| 70 | D, L-carnitine | 50.0 μ |
| 71 | folic acid | 5.0 μ |
| 72 | D,L-α-lipoic acid | 2.0 μ |
| 73 | menadione | 0.2 μ |
| 74 | nicotinic acid amide | 20.0 μ |
| 75 | pyridoxal-HCl | 5.0 μ |
| 76 | pyridoxine-HCl | 2.0 μ |
| 77 | riboflavin | 1.0 μ |
| 78 | rutine | 5.0 μ |
| 79 | thiamine-HCl | 5.0 μ |
| 80 | D,L-α-tocopheryl acetate | 1.0 μ |
| 81 | vitamin-A-acetate | 1.0 μ |
| 82 | vitamin $K_1$ | 0.2 μ |
| 83 | vitamin $B_{12}$ | 0.5 μ |
| 84 | vitamin U | 1.0 μ |
| 85 | cholesterine | 1.0 μ |
| 86 | coenzyme-$Q_{10}$ | 0.1 μ |
| 87 | linoleic acid | 1.0 μ |
| 88 | linolenic acid | 5.0 μ |
| 89 | oleic acid | 5.0 μ |
| 90 | ethanol | 1.0 m |
| 91 | pH 7.10 | — |
| 92 | concanavaline A | 50.0 n |

Manufacture and culture of the cells or leucocytes must be effected under sterile conditions. The culture is conducted for enough time to obtain a satisfactory yield of mediators. A duration of about 10 to 50 hours has proved suitable for this purpose. In the case of shorter times, the yield of mediators is too small, so that the method is uneconomic. With a culture duration of above about 50 hours on the other hand, the medium is exhausted and the cell begin to die off, so that no further increase in yield is to be expected.

The culture of the cells or leucocytes is carried out at a temperature of about 30 to 42° C., preferably of about 37° C. At lower temperatures the culture process is unsatisfactory, while at temperatures above 42° C. the cells or leucocytes are damaged. The culture is carried out at a concentration of about $10^6$ to $5 \times 10^8$ cells/ml, preferably up to $10^7$ to $10^8$ cells/ml. At lower cell concentrations the yield per volume unit of the culture solution is too low. As a result of culture volumes which are too high, the method becomes uneconomic. At a cell concentration of above $5 \times 10^8$ cells/ml depletion of nutrients in the medium occurs extremely rapidly.

The culture can be carried out in the atmosphere. Preferably however an increased carbon dioxide partial pressure is maintained above the culture, which can extend to about 10% by volume, particularly to about 2% by volume. The oxygen supplied to the culture is of great importance. It may for example be ensured by the introduction of air. In order to avoid contaminating the culture, the supplied air is preferably sterilised and heat-decontaminated, i.e. of endotoxins and other organic components. The solution may be stirred or shaken during culture. A lectin, preferably from canavalia ensiformis (Con A) is used as a cell stimulant.

In order to terminate the culture, the cells or leucocytes are centrifuged off from the culture solution, which is then prepared on the resulting mediators. In order to avoid damage of the cells and thus contamination of the culture solution by cell particles, the culture is centrifuged at a relatively low acceleration, i.e. about 300 to 400×g, After separation of the larger part of the cells from the residue, the latter is more appropriately again centrifuged at a higher acceleration, in order to remove residual suspended particles. The separated cells or leucocytes can either be again cultivated, cryopreserved or supplied for another use.

Apart from the culture of leucocytes, the bioactive RNP-morphogens according to the invention can also be obtained as inflammation tissue. Here they arise through the accumulation of leucocytes due to the inflammation process initiated by tissue damage. The inflammation tissue can be obtained in a conventional way and used for preparation of the RNP. To this end the inflammation tissue us homogenised in buffer solution and the soluble components (exudate) are separated from the insoluble structural components of the tissue.

Preferably, inflamed infarcted heart muscle tissue is used, which is formed by ligation of the left forward rising branch of the left coronary artery by means of a transfemoral catheter technique during 24 hours. The inflamed heart muscle portion containing leucocytes is separated at 0 to 4° C. from non-infarcted healthy tissue.

In order to isolate and obtain the bioactive RNP according to the invention, it is necessary to prepare an extremely large volume of culture solution. At the beginning of the purification process it is therefore necessary for practical reasons to carry out as effective as possible a reduction of the volume to be treated. In addition to the small amounts of generated substance, among which are mainly proteins, the culture solution contains the mixture of the components of the medium. More advantageously, therefore, in the first step of purification, separation of the resultant proteins from the components of the medium and simultaneously from the large volume of aqueous solution, is carried out. This may be effected by a selective salting-out of the proteins from the culture solution, which is achieved for example by the addition of a sulphate or phosphate. Thereafter precipitation of the proteins is carried out in accordance with the example of salting-out by addition of ammonium sulphate to the culture solution. By means of saturation of the culture solution with ammonium sulphate, the largest proportion of the resultant proteins, together with any serum albumin possibly contained, is precipitated out. After separation of the precipitate of substances, for example by centrifuging, this latter can be separated into its individual components in the way described hereafter, and the contained bioactive RNP can be obtained. The obtained excess contains, in addition to the soluble components of the medium, also the portion of the substances soluble in saturated ammonium sulphate solution, among which there is also found a portion of the bioactive RNP. The excess is concentrated and the substances obtained are obtained therefrom in the following way. When the protein-containing culture solution is mixed with ammonium sulphate up to saturation level, the larger portion of the accompanying proteins is precipitated out. In this way a protein mixture is obtained which consists of a number of different proteins and whose separation into individual components is consequently laborious. In a preferred embodiment of the method according to the invention, the protein mixture contained in the culture solution is therefore already separated into a plurality of fractions in the precipitation stage. This separation into a plurality of protein fractions is possible, as the individual proteins are precipitated out at different ammonium sulphate concentrations. Preferably, the culture solution is mixed, in the method according to the invention, in stages with ammonium sulphate up to specific degrees of saturation, proteins being precipitated out in each fraction of the portion, whose solubility product lies beneath the respective degree of saturation. By appropriate selection of the saturation thresholds of the individual fractions, a coarse separation into groups of proteins can be achieved during precipitation in the method according to the invention.

For example, the culture solution is firstly mixed up to a saturation of 35% with ammonium sulphate. The protein precipitate obtained in separated. Thereafter the degree of saturation of the residual solution is increased to 45%. A new protein precipitate forms, which is separated. Then the remaining solution is set to a saturation degree of 90%. The protein precipitate thus obtained is likewise separated. The solution remaining from this precipitation is for example concentrated by dehydration dialysis or ultrafiltration.

Salt precipitation of the proteins is carried out likewise, like the following purification, preferably at a temperature of about 0 to 10° C., particularly about 4° C. The solutions used for purification have a pH value between 5 and 9, particularly between 6 and 8. In order to achieve a constant pH of the solution, before salt precipitation a strong buffer, e.g. 0.1 mol/l phosphate buffer, is preferably added. In order to maintain the redox potential of the proteins, cysteine is preferably added to the solutions in a quantity of 0.001 mol/l. Sterile conditions are not necessary for the protein purification.

The proteins obtained during salt precipitation can be passed, after dissolution in a medium which does not damage proteins, directly to the purification and separation described hereafter. The residue of the last precipitation stage is concentrated, for example by dehydration dialysis or ultrafiltration. In this case all compounds with a molecular weight of greater than about 300 to 500 Daltons, i.e. all the proteins and peptides of this fraction, are quantitatively obtained as a dialysis residue.

The protein fractions obtained in the stage described above contain the bioactive RNP according to the invention in a mixture with numerous extraneous proteins (other secreted proteins, possibly serum, albumin and possibly CON). The extraneous proteins are present in a largely predominating amount in the mixtures. By means of a series of purification steps, the bioactive RNP must be enriched and freed from the extraneous proteins to such an extent that these latter no longer disturb their molecular biological specificity. The bioactive RNP themselves are likewise a class of materials which is separated into its individual specifically-active individual types.

In general, purification processes for proteins and other natural products consist of a sequence of combined separating methods, which utilise for separation differences in properties in molecular size, charge, shape, structural stability and molecular area between the agent sought and the accompanying extraneous materials. Accordingly, numerous combinations of the most varied separation methods can be produced for purification of a protein. For handling properties, technical feasibility, accessibility to automation and economy of a purification method as well as for the quality of the natural product sought, not only is the type of separation steps used of importance, but in particular their optimised design and their logical combination in a purification sequence within the framework of the structural stability and other structural parameters of the agent sought. This also means that even the utilisation of identical or similar separation principles (e.g. molecular screen filtration, dialysis, ion-exchange adsorption, etc.) but in differing combinations, can be decisive for the handling capacity and economy of the purification process. In specific cases the utilisation or omission of a single technique (e.g. hydroxylapatite chromatography, zone precipitation chromatography, etc.) at a specific point in the purification sequence or within a defined part sequence, is of extreme importance for quality of the agent sought and for the handling capacity and economy of its purification process. These general relationships and basic principles of purification of natural materials are clearly illustrated for example by the generally known fact that in an economically viable and technically feasible purification process for natural materials, a column chromatographic purification stage or a lyophilisation (freeze-drying) step is not appropriate, before the entire output volume or the output concentration of the accompanying extraneous components of the raw agent extract has not been reduced to at least $\frac{1}{500}$ to $\frac{1}{1000}$ by other method steps.

A plurality of purification stages, known individually per se in biochemistry, are available for purification of the individual protein fractions. Examples of such purification steps are: preparative and analytical molecular screen filtration, anion and cation exchanger chromatography, or one-pot adsorption methods, chromatography on hydroxylapatite, zone precipitation chromatography and circulatory or cascade molecular screen filtration.

Even when one of the named purification processes ia carried out only once, a considerable amount of accompanying proteins can be separated from the bioactive RNP. However, the substances obtained in the fractions, despite their different molecular weight, frequently adhere very intensely together. They are frequently incompletely separated in accordance with their molecular weight, for example in molecular screen filtration, by the existence of non-ideal equilibriums in protein polyelectrolytes. It is therefore recommended to carry out at least two of the named separation processes one after the other. Preferably, the protein fractions containing the bioactive RNP are subjected to at least three of the named purification processes in succession.

All combinations of the separation steps mentioned form the subject matter of the method according to the invention. It is in this case part of the general knowledge of the person skilled in the art that specific sequences of separating steps are less logical than other combinations. For example, the expert knows that in carrying out a preparative molecular screen filtration after an analytical molecular screen filtration, in addition to the cumbersome procedure, also a poorer overall result is obtained with respect to the separation effect than if the sequence is reversed.

Molecular screen filtration causes a separation of proteins in accordance with their molecular weight. As a predominating proportion of the accompanying extraneous proteins have a different molecular weight from the bioactive RNP, their separation may be achieved in this way. A hydrophilic molecular screen which swells in water is used to separate the substances according to their molecular weight. Examples of appropriate molecular screens are dextranes, cross-linked with epichlorydrine (Sephadex), agaroses (Ultrogels) cross-linked with acrylamide, and enmeshed acroamides (biogels), whose exclusion thresholds are higher than the separation thresholds used for separation.

If a plurality of separation stages are used, molecular screen filtration is preferably used as one of the first.

Depending on the ratio of length to diameter of the column used, and of the particle diameter of the gel matrix, which influence the theoretical plate number of the column, the molecular screen filtration is identified as "preparative", or "analytical". It is identified as "preparative", when the chromatography is carried out in columns with a dimensional ratio of length to diameter of up to 10:1 and a charge of up to ⅓ of the column content or with full utilisation of the entire matrix-typical separation volume. "Analytical" means a length-diameter ratio of about 10:1, preferably about 50:1, and a maximum charge of up to 3% of the column content, even with HPLC versions.

In preparative molecular screen chromatography, gel matrices are used with the largest possible particle size, in order to obtain rapid throughflow rates of the frequently rather viscous protein solutions with the lowest possible pressures. In analytical molecular screen filtration the particle size of the gel matrix is selected to be as small as possible, in order to achieve a maximum theoretical plate number of the column with a pressure which is utilisable technically and in terms of safety, and a flow speed of the mobile phase of 2 to 4 cm/h. These parameters are dependent on the gel matrix structure and differ from gel to gel.

If a plurality of preparative molecular screen filtrations are carried out in succession, the separation threshold can be selected to be gradated. Thereafter an analytical molecular screen filtration with correspondingly graded separation thresholds can be carried out. The exclusion threshold of the gel used must in any case be greater than about 10000 Daltons, in order to enable a volume distribution of the RNP between the stationary gel matrix phase and the mobile aqueous buffer phase.

The "exclusion threshold" identifies the hydrodynamic parameter of a dissolved particle, which corresponds to the pore size of the gel matrix. Particles with larger hydrodynamic parameter can no longer penetrate into the gel matrix (volume distribution coefficient $K_D=0$). The The "separation threshold" identifies a hydrodynamic parameter more appropriately fixed for separation of dissolved particles, which lies between a volume distribution coefficient $K_D=0$ and $K_D=1$.

For molecular screen filtration, the substances are applied, dissolved in a liquid not harmful to the substances, to the molecular screen. A more special example of a suitable solvent is 0.003 mol/l sodium-potassium phosphate solution with a content of 0.3 mol/l NaCl and 0.001 mol/l cysteine and a pH value of 7.4 After filtration, the fractions containing RNP are concentrated in the way described hereafter, and if necessary subjected to a further purification stage.

Suitable anion exchangers for purifying the substances are for example dextrane (Sephadex) or cellulose matrices cross-linked with epichloryhydrin, to which are coupled functional groups with anion exchange capacity. They may be used again after regeneration. Preferably used is a weak anion exchanger in Cl form, such as DEAE-Sephadex-A 50, pre-swelled and equilibrated in a buffer solution, and the treatment is carried out at a pH value of 8 to 10. A special example of such a buffer solution is 0.01 mol/l tris-HCl, containing 0.04 mol/l NaCl and 0.001 mol/l cysteine and having a pH value of 8.0.

When the anion exchanger is used the substance fraction has added thereto such an amount of anion exchanger as is sufficient for total adsorption of the RNP and of the positively adsorbing accompanying proteins. More conventionally two portions by volume of swollen anion exchanger per volume of concentrated protein fraction are sufficient for this. The reaction can be designed either as a chromatography process or as a more easily handled one-pot adsorption process. In the one-pot process the residual liquid with the negatively adsorbed proteins are separated from the anion exchanger charged with the positively adsorbed RNP and other substances, for example by filtration (in the chromatography column), decanting or centrifuging (in the one-pot process). The charged anion exchanger is freed, by washing with water or a salt solution, which has a maximum ion strength equivalent to 0.04 mol/l NaCl, preferably at most at about 15° C., of adhering, negatively adsorbed compounds. A special example for a salt solution suitable for washing out is the mentioned tris-HCl buffer solution with a pH value of 8.0.

The anion exchanger charged with RNP freed of negatively adsorbed compounds and other substances is now eluted with an aqueous salt solution harmless to proteins, which has an ion strength greater than corresponds to 0.04 mol/l NaCl and a pH value between 4.0 and 10.0. Preferably, a salt solution is used of high strength with a pH value of 5.0 to 7.0. A special example of such a salt solution is a 2.0 mol/l NaCl solution, buffered with 0.01 mol/l hyperazine HCl with a pH value of 6.5, and containing 0.001 mol/l cysteine.

If the anion exchanger reaction is designed as a chromatography process, elution of the RNP and other substances can be effected by a linear NaCl concentration gradient.

Suitable as cation exchangers for purification of the protein fraction are for example dextrane (Sephadex) or cellulose matrices cross-linked with epichloryhydrin, to which are coupled functional groups with cation exchange capacity. After use they may be used again by regeneration. Preferably, a weakly acidic cation exchanger in the $Na^+$ form, such as cm-Sephadex C-50, is used and the treatment is carried out at a pH value of 4 to 6. In order to simplify setting of the charge equilibria, the substance fractions can be diluted before treatment with the cation exchanger with a salt solution harmless to the proteins, which has a maximum ion strength equivalent to 0.04 mol NaCl/l. It can simultaneously serve to set the pH value. A special example of such a salt solution is 0.001 mol/l potassium phosphate acetate buffer solution with a content of 0.04 mol/l NaCl and a pH value of 4 to 6. This cation exchanger reaction can be designed both as a chromatography process and also as a technically easily-handled one-pot process.

The cation exchanger is added to the substance fraction in a quantity sufficient to adsorb the protein fraction. Conventionally sufficient for this is approximately two parts by volume of swelled ion exchanger per part by volume of protein fraction. Then the residual liquid is separated from the cation exchanger charged with the substances, for example by decanting or centrifuging. The charged cation exchanger is freed of adhering, non-adsorbed compounds by washing with water or a salt solution, which has a maximum ion strength equivalent to 0.04 mol/l NaCl, preferably at a pH value of about 4 to 6 and a maximum temperature of preferably about 15° C. A special example of a salt solution suitable for washing out is the above mentioned potassium phosphate acetate buffer solution with pH value 5.0.

The cation exchanger freed of negatively adsorbed compounds, and charged with substances, is now eluated with an aqueous salt solution harmless to proteins and nucleinic acids. A salt solution of high ion strength with a pH value of about 4 to 10 is preferably used for this purpose. Special examples of such salt solutions are an aqueous 0.5 mol/l potassium phosphate solution with pH value 6.5 to 7.5 or a 2 to 5 mol/l sodium chloride solution of the same pH value.

For chromatography on hydroxylapatite, any salts possibly present from preceding steps, e.g. ammonium sulphate and above all phosphates, are removed preferably by dialysis or ultrafiltration on a membrane with an exclusion threshold of 500 Daltons, before application onto the hydroxylapatite. Apart from the increase in viscosity due to foreign additives, however, only the phosphate concentration of the protein solution is critical for the success of chromatography on hydroxylapatite. Elution of the substances is effected through a sodium phosphate concentration gradient, which is preferably linear. The fractions containing RNP are collected and concentrated in the way to be described later.

The use of hydroxylapatite is of critical importance for obtaining the metal-containing RNP in a pure state with minimum stress on structures. For technical and economic reasons it is extremely difficult to subject large volumes of substances to chromatography on hydroxylapatite columns. On the one hand, at larger substance volumes hydroxylapatite has a tendency to clog and thus become unusable. On the other hand, hydroxylapatite is expensive, which invalidates its use on a greater scale. For this reason it is preferred in the method according to the invention to separate by means of appropriate process steps a large proportion of the accompanying extraneous proteins from the substance fractions containing the bioactive RNP as traces, before chromatography on hydroxylapatite, and in this way decisively to reduce the protein volume which must be applied to the hydroxylapatite column.

In zone precipitation chromatography (cf. J. Porath, Nature, volume 196 (1962), pages 47–48), protein impurities of bioactive RNP are separated by salting-out fractionation of the proteins by means of a salt concentration gradient.

The basic principles of protein separation by means of zone precipitation chromatography are various structurally defined reversible solubility properties of proteins and of RNP. They belong to the most sensitive molecular separation parameters and are frequently used as a criteria for proof of the molecular homogeneity of a protein. In this case temperatures and pH value, dimensions of the column, type of salt, form of gradient and charge of the column can be varied within a relatively wide range.

The temperature during zone precipitation chromatography can come to about 0 to 40° C. Preferred is a temperature range of about 0 to 10° C., particularly about 4 to 6° C. The pH value can lie between about 4 and 10; preferred is a pH value in the range of 6 to 8, particularly about 7. The ratio of length to diameter of the column used should be greater than about 10:1; a ratio of 30 to 100:1 is preferred, particularly about 50:1. All salts harmless to proteins and nucleinic acids can be considered in this embodiment. Examples of such salts are sodium-potassium phosphate, ammonium sulphate and sodium sulphate. Ammonium sulphate is preferably used.

The salt concentration gradient can be of any optional form, as long as the washing-out points of the proteins are separated in terms of the process path. Linear concentration gradients are preferred, particularly a rising linear concentration gradient of 25 to 100% ammonium sulphate saturation. Charging of the column comes to a maximum of about 5%, preferably about 1%.

Circulatory or cascade molecular screen filtration can be carried out under the conditions described above for analytical molecular screen filtration. The same molecular screens and the same column conditions can be used. Preferred is Sephadex G-50 at a length-diameter ratio of the column of at least about 50:1 and a charge of a maximum about 3% of the column content. As a solvent and for elution, the solvents used in analytical molecular screen filtration are preferably used.

In circulatory molecular screen filtration the eluate, at the fixed separation thresholds, is circulated back into the same column. In this way the process path of the molecules is differentially extended. In another embodiment, cascade molecular screen filtration, the eluate is passed, at the fixed separation thresholds, on to a new column with identical or similarly-defined parameters.

Between the purification stages explained above, the substance solutions containing bioactive RNP obtained, can be purified of undesired salts and concentrated to form subsequent separations of the proteins/RNP. This concentration (separation of the majority of the aqueous salt solution from the substances) can be achieved in various ways. For example, the bioactive RNP and the accompanying substances can be concentrated by ultrafiltration or dehydration dialysis on a membrane with an exclusion threshold of 500 Daltons or by lyophilisation. For this purpose a molecular screen filtration may also be used modified in a conventional manner by selection of the corresponding mobile phase. In molecular screen filtrations, preferably about 0.4 mol/l ammonium sulphate is added to the substance solution. In contrast to higher concentrations, ammonium sulphate in this concentration has an intense salting-in effect relative to proteins. By these measures, accordingly, the proteins are held in solution during molecular screen filtration. Furthermore, ammonium sulphate prevents bacterial growth and inhibits certain enzymes. In this way it contributes to stabilising the bioactive RNP, particularly when chromatography is carried out at higher temperatures (above about 20°) and under non-sterile conditions.

Temperature and pH conditions are not particularly critical when carrying out the purification stages. When it is intended to maintain the native conformation of the substances, it is recommended that a temperature in the range of about 0 to 8° C., preferably about 0 to 4° C., be maintained. Further, the separation and purification stages must be carried out under substantially physiological pH and salt conditions. A substantial advantage of the method according to the invention resides in the fact that maintaining these conditions is for the first time easily possible. In order to prevent oxidation, the substance solution is preferably also mixed with about 0.001 mol/l cysteine.

The bioactive RNP obtained may be stored in a buffered physiological salt solution, for example in 0.0015 mol/l sodium-potassium phosphate solution containing 0.15 mol/l (0.9%) NaCl and 0.001 mol/l cysteine and having a pH value of 7.4, after conventional filter sterilisation (pore width 0.2 $\mu$m) natively and biologically active also at room temperature (for at least 200 hours) or frozen at −25° C. (for at least 5 years). This stability of the bioactive RNP can be regarded among other things as one of the criteria for its highly pure condition.

The RNP according to the invention can also be produced by using chemically or biologically synthesised part sequences or parts and homologous sequences thereof. It is preferred to use the chemically or biologically synthesised oligonucleotide or antisense nucleotide sequences in vivo or in vitro, which code the part sequences given according to claim 1, with at least 6 bases in the PCR reaction, or the antisense bioprocess technology.

The examples serve to explain the invention. The examples describe how RNP morphogens are obtained proceeding from leucocytes from pig blood. The invention is however not restricted to this embodiment. Cells of the reticulo-endothelial system or inflammation, wound tissue or liquid (exudate) of other mammals can be used.

EXAMPLE 1

There is described the production of bioactive RNP from a culture solution of a mixed leucocyte population and the separation of the monocyte-CuRNP from the other components of the culture solution. All working steps are carried out at 0 to 8° C. in the presence of 0.001 mol/cysteine, where not otherwise indicated. Centrifuging is effected as described, either in one or two stages (as continuous flow centrifuging).

50 kg (about $10^{14}$) leucocyte are isolated as a mixed cell population of physiological composition from 10,000 litres of pig blood and cultivated in 20 batches of 2.5 kg (about $5 \times 10^{12}$ cells) under sterile conditions. The medium shown in Table 1 is for example used as a culture solution. 50 litres of culture medium per batch are used. The culture is carried out in glass vessels. Initial cell density is 108 cells/ml. The culture is maintained at 37° C. in an atmosphere of 1v/v % $CO_2$ for 40 hours. During this time the cell suspension is slowly stirred (60 rpm); during this time, sterile, pyrogen-free, water-washed fine (smaller than 1 mm) air bubbles (about 5 litres air/hour) and heat-decontaminated at about 500° C. in a quartz tube, are passed through. In addition to the oxygen partial pressure, the pH value (7.1) and the D-glucose level are measured and kept constant. The cells are stimulated during culture by a component in the culture medium of a polyvalent lectin (CON). The number, the differential and morphological viability (pigment exclusion test) of the cells are continuously determined with conventional methods of haematology and cell culture technology. The functional viability of the cells is measured on the basis of their motility and stimulability with chemokinetic and chemotactic proteins. Mitoses are determined by chromosome count. The morphological viability of the cells at the end of the biotechnical culture is greater than 85W. The overall cell loss (mainly granulocytes) during culture is at a maximum of 20%, which is normal for primary cell cultures.

The culture is terminated by separation of the cells from the remaining solution by 10 minutes, centrifuging at 500×g and at 10° C. The cells are washed twice with a salt solution containing 0.15 mol/l NaCl and 0.0015 mol/l potassium-sodium phosphate, and having a pH value of 7.1. They may be further used.

The culture solution is again centrifuged at 10000×g for 1 hour at 4° C. in order to remove suspended particles. The clear culture solution obtained (together with 1000 l with a content of about 1400 g proteins and other macromolecules) is directly subjected to the salting-out fractionation with ammonium sulphate.

1. First Step of Purification (salting-out fractionation)

The culture solution is mixed with 0.5 mol/l potassium sodium phosphate buffer solution up to a final concentration of 0.1 mol/l. Further, solid L-cysteine is added up to a concentration of 0.001 mol/l. The culture solution is then set to an ammonium sulphate saturation concentration of 35 by the addition of 199 g ammonium sulphate/l solution. During this addition the pH value of the solution is continuously monitored and held at 6.7 by the addition of 2 n ammonia. A portion of the proteins is precipitated out of the solution. The protein precipitate is separated from the residue containing dissolved substances by centrifuging for 1 hour at 10000×g. The protein fraction 1 is obtained as a protein sludge containing ammonium sulphate, which contains about 100 g protein.

The culture solution is then set to an ammonium sulphate saturation concentration of 45% by the addition of 60 g ammonium sulphate/l solution. During this addition the pH value of the solution is continuously monitored and held at 6.7 by the addition of 2 n ammonia. A further proportion of the proteins is precipitated out of the solution. The protein precipitate is separated from the residue containing dissolved substances by centrifuging for 1 hour at 10000×g. The protein raw fraction 2 is obtained as a protein sludge containing ammonium sulphate, and which contains about 60 g protein. The protein raw fraction 2 can likewise be separated and, after the process indicated above, can be processed in order to obtain its contents.

The culture solution is then set to an ammonium sulphate saturation concentration of 90% by addition of 323 g of ammonium sulphate/l solution. During this addition, the pH value of the solution is continuously monitored and held at 6.7 by the addition of 2 n ammonia. A further proportion of the proteins is precipitated out of the solution. The protein precipitate is separated from the residue containing dissolved substances by centrifuging for 1 hour at 10000×g. The protein raw fraction 3 is obtained as a protein sludge containing ammonium sulphate, and which contains about 1080 g proteins. The majority of the serum albumin is also located in this fraction. The protein raw fraction 3 is likewise processed after the process indicated above, in order to obtain its contents. The residue 4 of the raw fraction contains 160 g proteins and other macromolecules. Bioactive monocytary RNP is found in this residue.

The residue 4 containing protein is diluted with the same volume of buffer solution A (0.15 mol/l NaCl, 0.0015 mol/l potassium-sodium phosphate, 0.001 mol/L-cysteine; pH 7.4) to an ammonium sulphate saturation degree of 45% and a phosphate concentration of 0.05 mol/l. This solution is concentrated over a membrane with the exclusion threshold of 500 Daltons. The substances contained in the solution are obtained as a dialysis residue solution with a volume of 13 l (about 100 times concentration).

The residue solution is further purified separately.

The residue solution is purified in the way explained above, preparative molecular screen filtration being preceded in the sequence by anion exchanger chromatography. Moreover, there is used in the preparative molecular screen filtration and in the analytical circulatory molecular screen filtration, instead of Ultrogel AcA, a dextrane molecular screen matrix (Sephadex G-50) cross-linked with epichloryhydrin, with a particle size of 40 to 120 or 20 to 80 μm.

In preparative molecular screen filtration, the separation thresholds are set to 7000 to 3000 Daltons.

In chromatography on hydroxylapatite, RNP is eluted at a median phosphate concentration of 0.001 mol/l–1.0 mol/. In zone precipitation chromatography RNP is eluated in the front distribution. In analytical circulatory molecular screen filtration the eluate is circulated at a separation threshold of 7000.

About 8 mg RNP with a purity >95W are obtained.

EXAMPLE 2

3.5 kg (about $7 \times 10^{12}$) monocytes, obtained from pig blood, are cultivated under the conditions indicated in example 1. The cells are stimulated during culture. by a component in the culture medium of a polyvalent lectin (CON).

The RNP arising in the culture solution is isolated according to the method described in example 1 and obtained in a highly pure condition. Similar yields are achieved to those in example 1.

EXAMPLE 3

The production is described of bioactive RNP from an inflammation tissue and the separation of the RNP contained therein from the remaining components of the tissue. 500 g of infarcted, inflamed heart muscle tissue of the dog is used. The heart muscle tissue is comminuted in a meat grinder at 0 to 4° C., and mixed with a triple volume of its weight of a 0.05 mol/l potassium-sodium phosphate buffer solution, which contains 0.001 mol/l cysteine at a pH of 6.80. The suspension obtained is homogenised with a homogeniser (Ultraturax). Then the residue containing the soluble ingredients of the inflammation tissue is separated from the undissolved components by centrifuging at 10000×g. These operations are carried out at a temperature of 4° C. Then the solution obtained is centrifuged for 3 hours at 100000×g. The clear solution thus obtained is separated from the lipid layer floating thereon.

The clear solution obtained, containing RNP, is now subjected in accordance with example 1 to fractionated precipitation with ammonium sulphate. The concentrated residual solution obtained is prepared on the RNP according to example 1. About 0.03 mg RNP morphogen is obtained.

EXAMPLE 4

According to example 3, a homogenate of 500 g leucocytes is produced and suspended in the buffer solution indicated there. Preparation to the bioactive RNP contained in the leucocytes is effected according to example 1. In the leucocytes not cultivated under stimulation, only relatively few (about 1%) quantities of monocyto-RNP are obtained. The yields come to about 1 μg RNP.

What is claimed is:

1. An isolated ribonucleotide polypeptide ("RNP") containing a metal ion selected from the group consisting of Ca, Cu, and Zn, wherein the ribonucleotide portion of said RNP comprises:

AAAGAGAAAGCUGCUCCGAAGNCAG (SEQ ID NO:1).

the polypeptide portion of said RNP comprises all or part of the amino acid sequence:

NH$_2$-TKLEDHLEGIINIFHQYSVRLG (SEQ ID NO:3)

HYDTLIKRELKQLITKELPNTLKN

TKDQGTIDKIFQNLDANQDEQVSF

KEFVVLVTDVLITAHDNIHKE-COOH and wherein
the molecular mass of said RNP is about 40000 Daltons.

2. The ribonucleotide polypeptide according to claim 1, wherein said ribonucleotide polypeptide contains at least one of said metal ion in a RNP complex.

3. The ribonucleotide polypeptide according to claim 1, wherein said ribonucleotide polypeptide contains at least one modified base that is isoguanosine.

4. A method for producing an isolated ribonucleotide polypeptide ("RNP") wherein the ribonucleotide portion of said RNP comprises:

AAAGAGAAAGCUGCUCCGAAGNCAG (SEQ ID NO:1).

the polypeptide portion of said RNP comprises all or part of the amino acid sequence:

NH$_2$-TKLEDHLEGIINIFHQYSVRLG (SEQ ID NO:3)

HYDTLIKRELKQLITKELPNTLKN

TKDQGTIDKIFQNLDANQDEQVSF

KEFVVLVTDVLITAHDNIHKE-COOH wherein
the molecular mass of said RNP is about 40000, and wherein said method comprises:
   homogenizing or lysating cells, tissues, biological liquids, exudates, blood, leucocytes, inflammation tissues, hybridomes, biogenic recombinants, or mixtures thereof, and separating the resulting bioactive RNP from the homogenates or lysates.

5. The method according to claim 4, further comprising cultivating a mixed population of cells or tissue parts of a reticulo-endothelial system.

6. The method according to claim 4, further comprising cultivating the leucocytes in a fully synthetic, serum-free cell culture medium.

7. The method according to claim 4, further comprising stimulating the leucocytes during culturing by mitogens.

8. The method according to claim 7, further comprising stimulating the leucocytes by adding a polyvalent mitogen or endotoxin mitogen and thereby initiating an immunoreaction on the cell surface of the leucocytes.

9. The method according to claim 8, further comprising adding a lectin to stimulate the leucocytes.

10. The method according to claim 8, further comprising adding a lectin of canavalia ensiformis (Concanavalin A, ("CON")) stimulate the leucocytes.

11. The method according to claim 4, wherein culture of the leucocytes is carried out in a cell culture medium comprising: KCl 5.0 m mol/l; KH$_2$PO$_4$ 0.2 m mol/l; NaCl 120.0 m mol/l; Na$_2$HPO$_4$ 0.8 m mol/l; Na$_2$SO$_4$ 0.2 m mol/l; L-Ascorbic acid 0.2 m mol/l, Cholin Chloride 50.0 µmol/l; 2-Desoxy-D-ribose 5.0 µ; D-Galactose 0.5 m mol/l; D-Glucose 5.0 m mol/l; D-Glucurono-γ-lacton 0.1 m mol/l; Glycerine 50.0 µmol/l myo-Inosite 0.5 m mol/l; Na-Acetate 0.2 m mol/l; Na-Citrate 50.0 µmol/l; Na-Pyruvate 0.1 m mol/l; D-Ribose 20.0 µmol/l; Succinic acid 0.1 m mol/l; xylite 10.0 µmol/l; D-Xylose 20.0 µmol/l; CaCl$_2$ 2.0 m mol/l; MgCl$_2$ 1.0 m mol/l; NaHCO$_3$ 10.0 mol/l; Human serun albumin 7.7 µmol/l; Penicillin 1.0 µmol/l; Streptomycin 1.0 µmol/l; L-Glutamine 1.0 m mol/l; L-Alanine 0.2 m mol/l; L-Asparagine 0.1 m mol/l; L-aspartic acid 0.1 m mol/l; L-glutamic acid 0.1 m mol/l; glycine 0.2 m mol/l; L-proline 0.1 m mol/l; L-serine 0.1 m mol/l; L-arginine 0.4 m mol/l; 4-aminobenzoic acid 2.0 µmol/l; L-cysteine 0.2 m mol/l; L-hstidine 0.1 m mol/l; L-hydroxyproline 10.0 µmol/l; L-isoleucine 0.2 m mol/l; L-leucine 0.2 m mol/l; L-lysine-HCl 0.2 m mol/l; L-methionine 0.1 m mol/l; L-ornithine 50.0 µmol/l; L-phenylaline 0.1 m mol/l; sacosine 50.0 µmol/l; taurine 0.1 m mol/l; L-threonine 0.2 m mol/l; L-tryptophane 50.0 µmol/l; L-tyrosine 0.1 m mol/l; -valine 0.2 m mol/l; glutathion reduced 3.0 µmol/l; carnosine 5.0 µmol/l; mevalolactone 50 µmol/l; adenine 50.0 µmol/l; adenosine 50.0 µmol/l; cytidine 50.0 µmol/l; guanine 5.0 µmol/l; guanosine 20.0 µmol/l; hypoxanthine 5.0 µmol/l; 5-methylcytosine 5.0 µmol/l; thymidine 20.0 µmol/l; thymine 5.0 µmol/l; uracil 5.0 µmol/l; uridine 20.0 µmol/l; xanthine 5.0 µmol/l; biotine 1.0 µmol/l; D-Ca-pantothenate 5.0 mol/l; ergocalciferol 0.5 µmol/l; D,L-carnitine 50.0 µmol/l; folic acid 5.0 µmol/l; D,L-α-lipoic acid 2.0 µmol/l; menadione 0.2 µmol/l; nicotinic acid amide 20.0 µmol/l; pyridoxal-HCl 5.0 µmol/l; pyridoxine-HCl 2.0 µmol/l; riboflavin 1.0 µmol/l; rutine 5.0 µmol/l; thiamine-HCl 5.0 µmol/l; D,L-α-tocopheryl acetate 1.0 µmol/l; vitamine K$_1$ 0.2 µmol/l; vitamine B$_{12}$ 0.5 µmol/l; vitamin U 1.0 µmol/l; cholesterine 1.0 µmol/l; coenzyme-Q$_{10}$ 0.1 µmol/l; linoleic acid 1.0 µmol/l; linoleic acid 5.0 µmol/l; oleic acid 5.0 µmol/l; ethanol 1.0 m mol/l; pH7.10; and concanavaline A 50.0 n mol/l; which contains at least one defined protein, said protein is preferably serum albumin.

12. The method according to claim 4, wherein culturing of the leucocytes is carried out for about 40 hours at about 37° C. and a concentration of up to about 10$^7$ to 10$^8$ cells/ml culture solution under a CO$_2$ partial pressure of about 1% and with sufficient oxygen supply for the culture.

13. The method according to claim 4 further comprising terminating the culture by separation of the cells and/or tissue parts, by means of dialysis, ultrafiltration, salting-out from the residual culture solution, obtaining a plurality of substances contained in a second solution from homogenates, lysates or cell culture solutions, and obtaining the proportion of the substance soluble in a saturated salt solution by concentration of said second solution.

14. The method according to claim 13, wherein said salting-out is accomplished by the addition of amimonium sulphate.

15. The method according to claim 14, further comprising increasing the ammonium sulphate concentration of the solution in stages, separating precipitated substances after each addition of ammonium sulphate, and obtaining a plurality of raw fractions with staged solubility at different ammonium sulphate concentrations.

16. The method according to claim 15, wherein the ammonium sulphate concentration of the solution is set in stages to 35%, 45% and 90% saturation.

17. The method according to claim 16, further comprising concentrating the solution of the homogenates or lysate, or residue of the salting-out precipitation after said separation of the precipitated substance, by ultrafiltration or dialysis.

18. The method according to claim 17, further comprising separately processing the raw fractions obtained by staged salting-out, and a concentrated residue of the salting-out precipitation into isolated RNP.

19. The method according to claim 18, further comprising preparing the raw fractions and obtaining the isolated RNP by preparative and analytical molecular screen filtration, anion and cation exchanger chromatography or one-pot adsorption processes, chromatography on hydroxylapatite, zone precipitation chromatography and/or circulatory or cascade molecular screen filtration in a normal or HPLC form.

20. The method according to claim 19, further comprising carrying out at least two of the named purification stages in succession.

21. The method according to claim 19, further comprising carrying out at least three of the named purification stages in succession.

22. The method according to claim 4, further comprising, in order to obtain a monocytary RNP, a mixed leucocyte population or only monocytes are cultivated, the cells are stimulated by "CON" during the culture, the culture solution is mixed after termination of the culture with ammonium sulphate up to a saturation of 90%, the precipitated proteins are separated from the residue containing ammonium sulphate, the residue is concentrated, purified by preparative molecular screen filtration, an ion exchanger chromatography stage, a cation exchanger chromatography stage, a chromatography on hydroxylapatite, a zone precipitation chromatography and a cascade molecular screen filtration, and are obtained after separation of the accompanying extraneous substances in the eluate of the cascade molecular screen filtration, in a highly purified form.

23. The method according to claim 4, further comprising in order to obtain a leucocytary RNP, a mixed leucocyte population or only granulocytes are cultivated, the cells if necessary are stimulated during the culture by "CON", the culture solution is mixed after termination of the culture with ammonium sulphate up to a saturation of 35%, the precipitated proteins are separated from the residue containing ammonium sulphate, are re-dissolved and purified by an anion exchanger chromatography stage, a preparative molecular screen filtration, a cation exchanger chromatography stage, a chromatography on hydroxylapatite, a zone precipitation chromatography and a cascade molecular screen filtration, and, after separation of the accompanying extraneous proteins, the leucocytary RNP is obtained in a highly purified form in the eluate of the cascade molecular screen filtration.

24. The method according to claim 4, further comprising applying the soluble proportion of a leucocyte of inflammation tissue homogenate from a natural or recombinant cell form instead of a culture solution of the leucocytes.

25. A method of producing an isolated ribonucleotide polypeptide ("RNP") wherein the ribonucleotide portion of said RNP comprises:

AAAGAGAAAGCUGCUCCGAAGNCAG (SEQ ID NO:1).

the polypeptide portion of said RNP comprises all or part of the amino acid sequence:

NH₂-TKLEDHLEGIINIFHQYSVRLG (SEQ ID NO:3)

HYDTLIKRELKQLITKELPNTLKN

TKDQGTIDKIFQNLDANQDEQVSF

KEFVVLVTDVLITAHDNIHKE-COOH wherein
the molecular mass of said RNP is about 40000, and wherein said method comprises:
   producing RNP from said ribonucleotide portion and said polypeptide portion, wherein said ribonucleotide portion or said polypeptide portion is chemically and/or biomolecularly synthesised.

26. A method for producing an isolated ribonucleotide polypeptide ("RNP") wherein the ribonucleotide portion of said RNP comprises:

AAAGAGAAAGCUGCUCCGAAGNCAG (SEQ ID NO:1).

the polypeptide portion of said RNP comprises all or part of the amino acid sequence:

NH₂-TKLEDHLEGIINIFHQYSVRLG (SEQ ID NO:3)

HYDTLIKRELKQLITKELPNTLKN

TKDQGTIDKIFQNLDANQDEQVSF

KEFVVLVTDVLITAHDNIHKE-COOH wherein the molecular mass of said RNP is about 40000, and wherein said method comprises: cultivating the cells or tissues and separating the resulting bioactive RNP from the residual culture solution.

27. The method according to claim 26, further comprising cultivating a mixed population of cells or tissue parts of a reticulo-endothelial system.

28. The method according to claim 26, further comprising cultivating the leucocytes in a fully synthetic, serum-free cell culture medium.

29. The method according to claim 26, further comprising stimulating the leucocytes during culturing by mitogens.

30. The method according to claim 29, further comprising stimulating the leucocytes by adding a polyvalent mitogen or endotoxin mitogen and thereby initializing on immunoreaction on the cell surface of the leucocytes.

31. The method according to claim 30, further comprising adding a lectin to stimulate the leucocytes.

32. The method according to claim 30, further comprising adding a lectin of canavalia ensiformis (Concanavalin A, ("CON")) to stimulate the leucocytes.

33. The method according to claim 26, wherein culture of the leucocytes is carried out in a cell culture medium comprising: KCl 5.0 m mol/l; KH₂PO₄ 0.2 m mol/l; NaCl 120.0 m mol/l; Na₂HPO₄ 0.8 m mol/l; NA₂SO₄ 0.2 m mol/l; L-Ascorbic acid 0.2 m mol/l; Cholin Chloride 50.0 μmol/l; 2-Desoxy-D-ribose 5.0 μ; D-Galactose 0.5 m mol/l; D-Glucose 5.0 m mol/l; D-Glucurono-γ-lacton 0.1 m mol/l; Glycerine 50.0 μmol/l; myo-Inosite 0.5 m mol/l; Na-Acetate 0.2 m mol/l; Na-Citrate 50.0 μmol/l; Na-Pyruvate 0.1 m mol/l; D-Ribose 20.0 μmol/l; Succinic acid 0.1 m mol/l; xylite 10.0 μmol/l; D-Xylose 20.0 μmol/l; CaCl₂ 2.0 m mol/l; MgCl₂ 1.0 m mol/l; NaHCO₃ 10.0 m mol/l; Human serun albumin 7.7 μmol/l; Penicillin 1.0 μmol/l; Streptomycin 1.0 μmol/l; L-Glutamine 1.0 m mol/l; L-Alanine 0.2 m mol/l; L-Asparagine 0.1 m mol/l; L-aspartic acid 0.1 m mol/l; L-glutamic acid 0.1 m mol/l; glycine 0.2 m mol/l; L-proline 0.1 m mol/l; L-serine 0.1 m mol/l; L-arginine 0.4 m mol/l; 4-aminobeneoic acid 2.0 μmol/l; L-cysteine 0.2 m mol/l; L-hstidine 0.1 m mol/l; L-hydroxyproline 10.0 μmol/l; L-isoleucine 0.2 m mol/l; L-leucine 0.2 m mol/l; L-lysine-HCl 0.2 m mol/l; L-methionine 0.1 m mol/l; L-omithine 50.0 μmol/l; L-phenylaline 0.1 m mol/l; sarcosine 50.0 μmol/l; taurine 0.1 m mol/l; L-threonine 0.2 m mol/l; L-tryptophane 50.0 μmol/l; L-tyrosine 0.1 m mol/l; -valine 0.2 m mol/l; glurathion reduced 3.0 μmol/l; carnosine 5.0 μmol/l; mevalolactone 5.0 μmol/l; adenine 50.0 μmol/l; adenosine 50.0 μmol/l; cytidine 50.0 μmol/l; guanine 5.0 μmol/l; guanosine 20.0 μmol/l; hypoxanthine 5.0 μmol/l; 5-methylcytosine 5.0 μmol/l; thymidine 20.0 μmol/l; thymine 5.0 μmol/l; uracil 5.0 μmol/l; uridine 20.0 μmol/l; xanthine 5.0 μmol/l, biotine 1.0 μmol/l; D-Ca-pantothenate 5.0 mol/l; ergocalciferol 0.5 μmol/l; D,L-carninine 50.0 μmol/l; folic acid 5.0 μmol/l; D,L-α-lipoic acid 2.0 μmol/l; menadione 0.2 μmol/l; nicotinic acid amide 20.0 μmol/l; pyridoxal-HCl 5.0 μmol/l; pyridoxine-HCl 2.0 μmol/l; riboflavin 1.0 μmol/l; rutine 5.0 μmol/l; thiamine-HCl 5.0 μmol/l; D,L-α-tocopheryl acetate 1.0 μmol/l; vitamin K₁ 0.2 μmol/l; vitamine B₁₂ 0.5 μmol/l; vitamin U 1.0 μmol/l; cholesterine 1.0 μmol/l; coenzyme-Q₁₀ 0.1 μmol/l; linoleic acid 1.0 μmol/l; linoleic acid 5.0 μmol/l; oleic acid 5.0 μmol/l; ethanol 1.0 m mol/l; pH7.10; and concanavaline A 50.0 n mol/l; which contains at least one defined protein, said protein is preferably serum albumin.

34. The method according to claim 26, wherein culturing of the leucocytes is carried out for about 40 hours at about 37° C. and a concentration of up to about 10⁷ to 10⁸ cells/ml culture solution under a CO₂ partial pressure of about 1% and with sufficient oxygen supply for the culture.

35. The method according to claim 26 further comprising terminating the culture by separation of the cells and/or tissue parts, by means of dialysis, ultrafiltration, salting-out from the residual culture solution, obtaining a plurality of substances contained in a second solution from homogenates, lysates or cell culture solutions, and obtaining the proportion of the substance soluble in a saturated salt solution by concentration of said second solution.

36. The method according to claim 35, wherein said salting-out is accomplished by the addition of ammonium sulphate.

37. The method according to claim 36, further comprising increasing the ammonium sulphate concentration of the solution in stages, separating precipitated substances after each addition of ammonium sulphate, and obtaining a plurality of raw fractions with staged solubility at different ammonium sulphate concentrations.

38. The method according to claim 37, wherein the ammonium sulphate concentration of the solution is set in stages to 35%, 45% and 90% saturation.

39. The method according to claim 38, further comprising concentrating the solution of the homogenates or lysate, or residue of the salting-out precipitation after said separation of the precipitated substance, by ultrafiltration or dialysis.

40. The method according to claim 39, further comprising separately processing the raw fractions obtained by staged salting-out, and a concentrated residue of the salting-out precipitation into isolated RNP.

41. The method according to claim 40, further comprising preparing the raw fractions and obtaining the isolated RNP by preparative and analytical molecular screen filtration, anion and cation exchanger chromatography or one-pot adsorption processes, chromatography on hydroxylapatite, zone precipitation chromatography and/or circulatory or cascade molecular screen filtration in a normal or HPLC form.

42. The method according to claim 41, further comprising carrying out at least two of the named purification stages in succession.

43. The method according to claim 41, further comprising carrying out at least three of the named purification stages in succession.

44. The method according to claim 26, further comprising, in order to obtain a monocytary RNP, a mixed leucocyte population or only monocytes are cultivated, the cells are stimulated by "CON" during the culture, the culture solution is mixed after termination of the culture with ammonium sulphate up to a saturation of 90%, the precipitated proteins ale separated from the residue containing ammonium sulphate, the residue is concentrated, purified by preparative molecular screen filtration, an ion exchanger chromatography stage, a cation exchanger chromatography stage, a chromatography on hydroxylapatite, a zone precipitation chromatography and a cascade molecular screen filtration, and are obtained after separation of the accompanying extraneous substances in the eluate of the cascade molecular screen filtration, in a highly purified form.

45. The method according to claim 26, further comprising in order to obtain a leucocytary RNP, a mixed leucocyte population or only granulocytes are cultivated, the cells if necessary are stimulated during the culture by "CON", the culture solution is mixed after termination of the culture with ammonium sulphate up to a saturation of 35%, the precipitated proteins are separated from the residue containing ammonium sulphate, are re-dissolved and purified by an anion exchanger chromatography stage, a preparative molecular screen filtration, a cation exchanger chromatography stage, a chromatography on hydroxylapatite, a zone precipitation chromatography and a cascade molecular screen filtration, and, after separation of the accompanying extraneous proteins, the leucocytary RNP is obtained in a highly purified form in the eluate of the cascade molecular screen filtration.

46. The method according to claim 26, further comprising applying the soluble proportion of a leucocyte of inflammation tissue homogenate from a natural or recombinant cell form instead of a culture solution of the leucocytes.

* * * * *

```
                        SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (ii) MOLECULE TYPE: other nucleic acid (viii) POSITION IN GENOME:
         (C) UNITS: bp (xi) SEQUENCE DESCRIPTION: SEQ ID NO: 1:

AAAGAGAAAG CUGCUCCGAA GNCAG                                              25

(2) INFORMATION FOR SEQ ID NO: 2:

(i) SEQUENCE CHARACTERISTICS:
         (A) LENGTH: 91 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO: 2:

Thr Lys Leu Glu Asp His Leu Glu Gly Ile Ile Asn Ile Phe His Gln
1               5                  10                  15

Tyr Ser Val Arg Leu Gly His Tyr Asp Thr Leu Ile Lys Arg Glu Leu
            20                  25                  30

Lys Gln Leu Ile Thr Lys Glu Leu Pro Asn Thr Leu Lys Asn Thr Lys
        35                  40                  45

Asp Gln Gly Thr Ile Asp Lys Ile Phe Gln Asn Leu Asp Ala Asn Gln
    50                  55                  60

Asp Glu Gln Val Ser Phe Lys Glu Phe Val Val Leu Val Thr Asp Val
65                  70                  75                  80

Leu Ile Thr Ala His Asp Asn Ile His Lys Glu
                85                  90

(2) INFORMATION FOR SEQ ID NO: 3:

(i) SEQUENCE CHARACTERISTICS:
```

-continued

```
        (A) LENGTH: 273 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 3:

ACCAAGCTGG AGGACCACCT GGAGGGCATC ATCAACATCT TCCACCAGTA CTCTGTGCGG      60

CTGGGCCACT ATGACACCCT GATCAAGCGG GAGCTGAAGC AGCTGATCAC CAAGGAGCTG     120

CCCAACACCC TGAAGAACAC CAAGGACCAG GGCACCATTG ACAAGATCTT CCAGAACCTG     180

GATGCCAACC AGGATGAGCA GGTGTCCTTC AAGGAGTTTG TGGTGCTGGT GACAGATGTG     240

CTGATCACAG CCCATGACAA CATCCACAAG GAG                                  273

(2) INFORMATION FOR SEQ ID NO: 4:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 4:

AAAGAGAAAG CNGCNGCNCC GAAGNCAGCT GNCTTCGGNG CNGCTTTCTC TTT              53
```